(12) United States Patent
Boyd et al.

(10) Patent No.: US 11,229,941 B1
(45) Date of Patent: Jan. 25, 2022

(54) RADIAL COMPRESSION MECHANISM

(71) Applicant: Blockwise Engineering LLC, Tempe, AZ (US)

(72) Inventors: Jordan Bradley Boyd, Phoenix, AZ (US); Ed Goff, Phoenix, AZ (US); Jeremiah J. Warriner, Tempe, AZ (US)

(73) Assignee: Blockwise Engineering LLC, Tempe, AZ (US)

( * ) Notice: Subject to any disclaimer, the term of this patent is extended or adjusted under 35 U.S.C. 154(b) by 104 days.

(21) Appl. No.: 16/391,281

(22) Filed: Apr. 22, 2019

(51) Int. Cl.
*B21D 39/04* (2006.01)
*A61F 2/95* (2013.01)

(52) U.S. Cl.
CPC .............. *B21D 39/048* (2013.01); *A61F 2/95* (2013.01); *A61F 2/9522* (2020.05)

(58) Field of Classification Search
CPC .................................................. B21D 39/048
USPC ......................................................... 72/402
See application file for complete search history.

(56) References Cited

U.S. PATENT DOCUMENTS

| | | | |
|---|---|---|---|
| 6,651,478 B1* | 11/2003 | Kokish | A61F 2/9524 72/402 |
| 7,152,452 B2 | 12/2006 | Kokish | |
| 7,530,253 B2* | 5/2009 | Spenser | A61F 2/2412 72/402 |
| 7,618,252 B1 | 11/2009 | Goff | |
| 8,056,218 B2 | 11/2011 | Nickol et al. | |
| 8,245,559 B1* | 8/2012 | Warriner | B21J 9/06 72/402 |
| 9,757,232 B2 | 9/2017 | Peterson et al. | |
| 9,821,363 B2* | 11/2017 | Goff | B21J 7/16 |
| 2008/0053182 A1* | 3/2008 | Goff | A61F 2/95 72/354.2 |

* cited by examiner

*Primary Examiner* — Adam J Eiseman
*Assistant Examiner* — P Derek Pressley
(74) *Attorney, Agent, or Firm* — Invention To Patent Services; Alex Hobson

(57) ABSTRACT

A radial compression mechanism incorporates a plurality of compression die assemblies arranged radially about and forming a central cylindrical cavity. The die assemblies are coupled to a cam plate by a cam bearing retained in cam guide slots in the cam plate. The cam plate is configured to rotate about the central axis of the central cylindrical cavity and thereby rotate the plurality of compression dies about the central axis. The plurality of dies are constrained by a stationary guide slot configured in the housing of the radial compression mechanism and this stationary guide slot forces the compression dies to move radially inward to close the cylindrical cavity. Therefore, the compression dies both rotate about the central cylindrical cavity and move radially inward to close the cylindrical cavity. This arrangement and die displacement mechanism reduces the size or area required by the dies. Therefore the mechanism can be made smaller.

14 Claims, 9 Drawing Sheets

RADIAL COMPRESSION MECHANISM

BACKGROUND OF THE INVENTION

Field of the Invention

This invention generally relates to radial compression mechanisms and more specifically to mechanisms for compressing devices such as stents, catheters, balloons, and the like.

Background

In the manufacture and testing of medical devices, mechanisms are used to radially compress cylindrical devices such as stents, balloons, and catheters. For example, installation of a stent onto a catheter balloon is typically done by compressing the stent radially inward onto the balloon with enough pressure to permanently deform the stent to a smaller diameter and to slightly embed the metal stent into the plastic balloon. In another example, a polymer catheter balloon is compressed radially after pleating to wrap it tightly around the catheter shaft. In another example, a self-expanding stent is radially compressed to insert it into a sheath or delivery system. In an example of medical device testing, a stent is radially compressed while the required force is measured, in order to measure the stent's functional relationship between diameter and radial force.

A first type of prior art device includes a radial compression mechanism wherein several similar wedge-shaped dies with planar surfaces are arranged to form an approximately cylindrical central cavity; the wedges being hinged and driven in unison to change the diameter of the cavity. A mechanism of this type is illustrated in FIGS. 1 through 5. Examples of this mechanism are the Crimpfox tool sold by Phoenix Contact GmbH 7 Co. KG (CRIMPFOX UD 6-6, Part Number 1206366), and the "segmental compression mechanism" marketed by Machine Solutions Incorporated, and described in U.S. Pat. No. 6,968,607. In this type of mechanism, the working surfaces of the dies have a wedge shape with two planar surfaces meeting at the tip. A shortcoming of this type of mechanism is that there exists a gap between adjacent wedges, the size of which varies with the diameter of the cavity in an undesirable way. Typically, the mechanism is specifically designed to provide a desired range of cavity diameters. At the lowest and highest diameters, the dies are tightly wedged against each other (zero gap). As the diameter is increased from the lowest, the gap increases until it reaches a maximum, then decreases until it becomes zero again at the highest diameter, as illustrated graphically in FIG. 5 of U.S. Pat. No. 6,968,607. The diameter range and gap, as a function of diameter, depend on the specific design of the mechanism, particularly the location of the hinge point of the dies and the diameter of the circle formed by all of the die hinge points in the mechanism. A larger diameter of the hinge point circle results in a smaller maximum gap for a given diameter range. The strict design tradeoffs for this type of mechanism results in a mechanism that must be large to provide a small maximum gap for a given diameter range, or a mechanism that must have a large gap to provide the same diameter range in a small size. Large gaps between the wedges are a disadvantage because parts of the compressed device may go into the gaps. For example, the metal struts of a stent can move into the gap and be damaged.

A second type of prior art device includes a radial compression mechanism wherein several similar wedge-shaped dies with planar surfaces are arranged to form an approximately cylindrical central cavity, the wedges being attached to linear guides that constrain each die individually to move linearly relative to a stationary part, the dies being driven in unison to change the diameter of the central cavity. Each die's motion path is constrained when assembled to the stationary part, even when the other dies are not present. The dies are guided only by the linear guides, and not by neighboring dies. Examples of this mechanism include the mechanism taught by Kokish in U.S. Pat. No. 6,651,478, or the mechanism marketed by Interface Catheter Solutions as part of the model DFW-1000 balloon fluter-wrapper machine. In this type of mechanism, the working surfaces of the dies have a wedge shape with two planar surfaces meeting at the tip. The linear motion of the wedges in this mechanism provides a wedge-to-wedge gap that is constant, independent of the cavity diameter, and may be designed to be any desired size, see FIG. 10 of U.S. Pat. No. 6,651,478. A shortcoming of this mechanism is that it typically does not provide a sufficiently accurate positional relationship of the wedge-shaped working ends of the dies. Accurate positional relationship of the dies is important so that the central cavity remains approximately round and provides even compression around the circumference of the compressed device, and so that the largest die-to-die gaps aren't much larger than the average. Each die is carried on its own linear guide, all of the guides are attached to a plate or base, and another rotating part such as a cam must be used to impose motion in unison. Therefore, many parts and attachments may influence the accuracy (roundness) of the central cavity. Medical device manufacturing and testing often require an accurately round cavity at diameters as small as 0.3 mm., which this type of mechanism is typically unable to achieve because of dimensional variability of the many parts.

A third type of prior art device is a radial compression mechanism wherein several similar wedge shaped dies with planar surfaces are arranged to form an approximately cylindrical central cavity, the wedges are movably mounted for reciprocal movement. Cam followers are affixed to the dies. First cam surfaces are affixed relative to the housing and second cam surfaces are movably mounted relative to the housing. Each cam follower engages a first cam surface to define a first position control constraint, and a second cam surface to define a second position control constraint. Each die has a position relative to each adjacent die and the coaxial central cavity that is controlled by the first position control constraint and the second position control constraint. The first position control constraint and the second position control constraint fully constrain each die ensuring that the motion of each die is not influenced by adjacent dies. An example of this mechanism is described in U.S. Pat. No. 8,245,559 B1 and is marketed as the Twin-Cam radial compression mechanism by Blockwise Engineering. In this type of mechanism, the working surfaces of the dies have a wedge shape with two planar surfaces meeting at the tip. The dies move in a linear direction relative to adjacent dies and in a well-defined but nonlinear path relative to the first cam surface on the housing. The linear motion of the dies relative to each adjacent wedge in this mechanism provides a wedge-to-wedge gap that is constant, independent of the cavity diameter, and may be designed to be any desired size. A shortcoming of this mechanism is that it typically does not provide a sufficiently accurate positional relationship of the wedge-shaped working ends of the dies. The gap between adjacent dies at the working end is influenced by the positional accuracy between each die and the adjacent die but because motion of each die is controlled by the first position control constraint and the second position control constraint, and not the adjacent dies, the positional accuracy between the adjacent die and the corresponding die-die gap is typically too large. This positional inaccuracy leads to a larger die-die gap between adjacent dies and a more inconsistent average die-die gap for the machine as a whole.

A fourth type of prior art device is a radial compression mechanism wherein a plurality of dies are constrained by bearing surfaces between each adjacent die and a pair of spaced apart stationary plates with a generally polygonal cut-out. Each side of the polygonal shape forms a second bearing surface. The dies have planar surfaces that form an approximately cylindrical-shaped central cavity, with the dies being driven in unison to change the diameter of the central cavity. A mechanism of this type is described in U.S. Pat. No. 8,245,559 B1, and is marketed by Blockwise Engineering LLC as the "Alpha-Crimp" mechanism. This type of mechanism has an important advantage over the first type of prior art: constant die-to-die gaps that do not vary with opening diameter. It also has an important advantage over the second and third types of prior art: it can be manufactured with die-to-die gaps smaller and more precise, on the order of 0.01 mm.

It would be highly advantageous, therefore, to remedy the foregoing and other deficiencies inherent in the prior art.

SUMMARY OF THE INVENTION

The invention is directed to a radial compression mechanism that comprises a plurality of dies configured in a circular array, each having a working surface that cooperates with the other dies to form a central cavity having a central axis that is configured to open and close about the central axis. Adjacent dies form interface surfaces that constrain the dies to have linear motion relative to adjacent dies. A stationary housing has a cam guide that guides the plurality of dies to move from an open position to a closed position. The cam guides may be recesses or slots to receive a cam interface, such as a pin or post therein and a bearing may be configured to provide smooth and low friction guided motion along the cam guide. A cam guide may be a raised surface or rail and a cam interface may move or roll along or over the raised cam guide.

Rolling or sliding surfaces between adjacent dies constrain the dies to have linear motion relative to adjacent dies. Linear motion is defined as a sliding motion between the planar surfaces of adjacent dies. It should be noted that a wide variety of rolling elements may be used in the interface surfaces including die bearings, rolling cylinders, commonly known as needle rollers, balls, or a combination of these elements. A low friction surface may be configured between compression dies in the interface surface and may include low friction polymers, such as Teflon, hydrogels, and may include a liquid lubricant, such as an oil or polymer fluid.

In an exemplary embodiment, the die assemblies are coupled to a cam plate by a cam bearing or pin retained in cam guide slots or surfaces in the cam plate. The cam plate is configured to rotate about the central axis of the central cylindrical cavity and thereby move the die assemblies in unison along the path defined by the die-to-die linear guidance and the die-to-housing cam guidance, thereby opening or closing the central cavity.

An exemplary compression die assembly comprises die bearing arms that extend from either end of the compression dies and engage with cam guides, such as slots or recesses in both the housing and the rotating cam plate. A compression die assembly may be a one-piece unit, made from a single piece of material including the compression die portion and the die bearing arms, or the die bearing arm may be coupled to the compression dies by a fastener, for example. The coupling between the die assemblies and both the housing plate and the cam plate may be embodied by any common type of cam follower mechanism, such as cam follower bearings following slots or surfaces, ball bearings following slots or surfaces, plain bearings following slots or surfaces, or pins following slots or surfaces.

The shape of the slots in the rotating cam plate determine the relationship between the diameter of the center cavity and the position of the rotating cam plate. In the preferred embodiment, the rotating cam plate is actuated through an actuator arm to which a force is applied by. A mechanical advantage may be produced by the actuator arm and is the ratio of the radial force applied to the article in the central cylindrical cavity per amount of force applied by the actuator. The shape of the slots in the rotating cam plate are generally arcuate, and may be designed to achieve a particular mechanical advantage, including mechanical advantage that varies as function of cavity diameter. Longer slots in the rotating cam, correspond to a higher mechanical advantage as the mechanism moves from a larger diameter to a smaller diameter central cylindrical cavity. The shape of the slot in the stationary housing plate determines the relationship between cavity diameter and the rotation angle of the lot of dies. The slot may be designed to achieve any relationship between cavity diameter and rotation angle of the lot of dies that is practical or driven by the needs of the designer. The length and shape of the slot in the stationary plate can be modified to determine this relationship, allowing for greater design freedom of the mechanism.

In an exemplary embodiment, the compression dies are wedge shaped and have a working surface extending inward to form the cylindrical cavity and a back surface, opposing said working surface. Adjacent compression dies may move along interface surfaces between the working and back surfaces. In an exemplary embodiment, bearings are configured in the interface surfaces to reduce friction and enable smooth compression of articles within the cylindrical cavity. A bearing race may extend along a portion of the back surface of the compression dies and die bearings may be configured in this race. The die bearings may be slightly larger in diameter to the race dimension, or race offset dimension, and the difference in the race offset dimension and bearing diameter may determine the die gap, the gap between the interface surface of adjacent dies. A die bearing may be a ball bearing or a needle bearing, or any other suitable bearing assembly that retains the bearings in the bearing race. A die gap may be very small, such as no more than about 0.2 mm, no more than about 0.1 mm, no more than about 50 um, no more than 25 um, no more than 10 um and any range between and including the gap values provided. A small gap may be desired for certain articles that are compressed in the radial compression machine, such as stents having small diameter wires. Note that other friction reduction materials may be configured between interface surface of the compression dies and may be configured in races along the interfaces.

An exemplary cam plate may comprise a cam drive mechanism that is configured to rotate the cam about the central axis. A cam actuator may be a portion of the cam that extends radially outward from the cam. A cam actuator may be coupled with a drive mechanism to rotate the cam or the cam may be actuated manually. In an exemplary embodiment, a cam drive mechanism comprises an electric motor, a pneumatic actuator and the like. In an exemplary embodiment an electrical motor, such as a stepper motor, is coupled to the cam by gears, chain or belt drive, or screw drive.

An exemplary radial compression mechanism comprises a plurality of compression die assemblies and compression dies including three or more, five or more, eight or more, ten or more, about fifteen or more and any range between and including the number of compression dies provided. The cylindrical shape of the cylindrical cavity will be more cylindrical with a higher number of compression dies and the complexity and cost to produce the radial compression mechanism is increased with more compression die assemblies.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
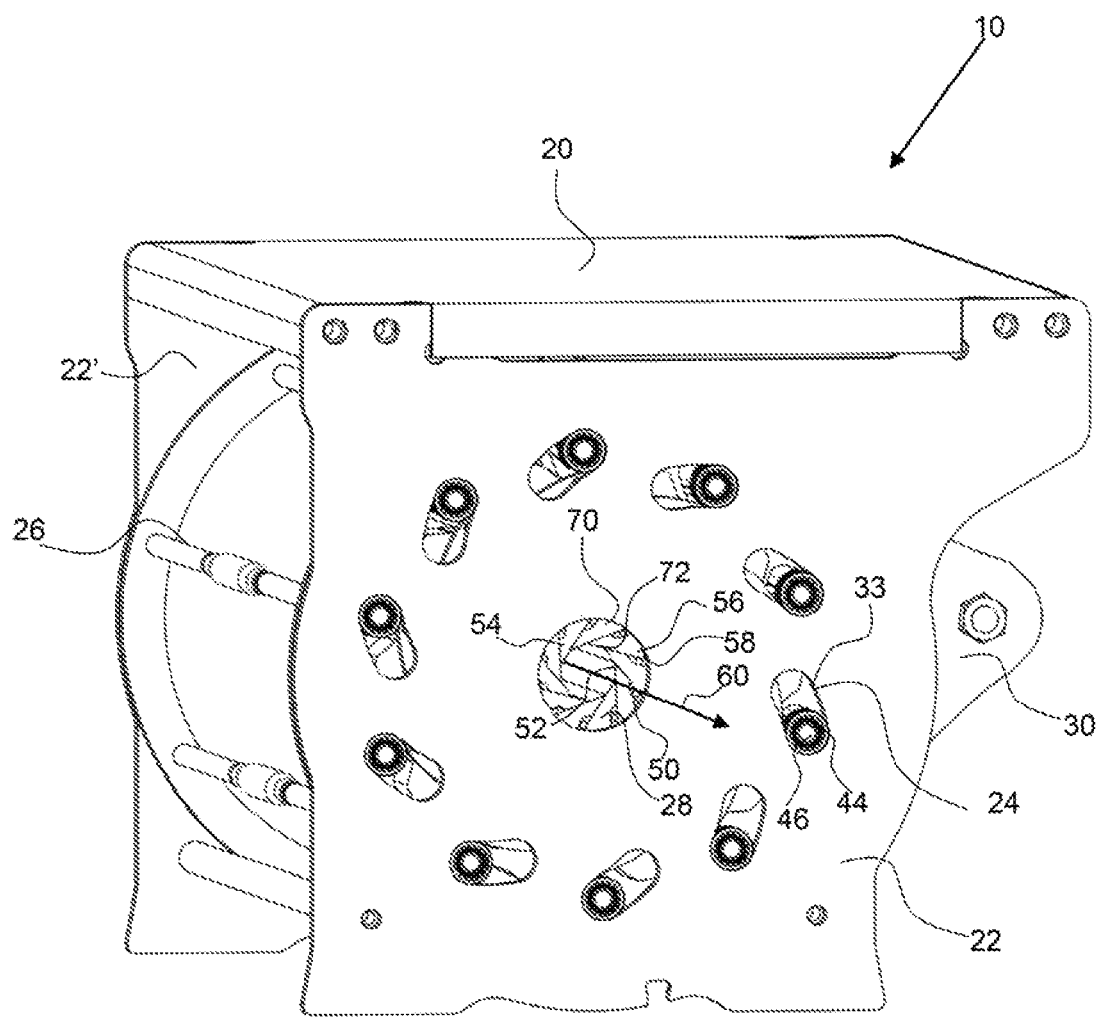
FIG. 1 shows a perspective receiving-side view of an exemplary radial compression mechanism in a partially open orientation.
Figure 2:
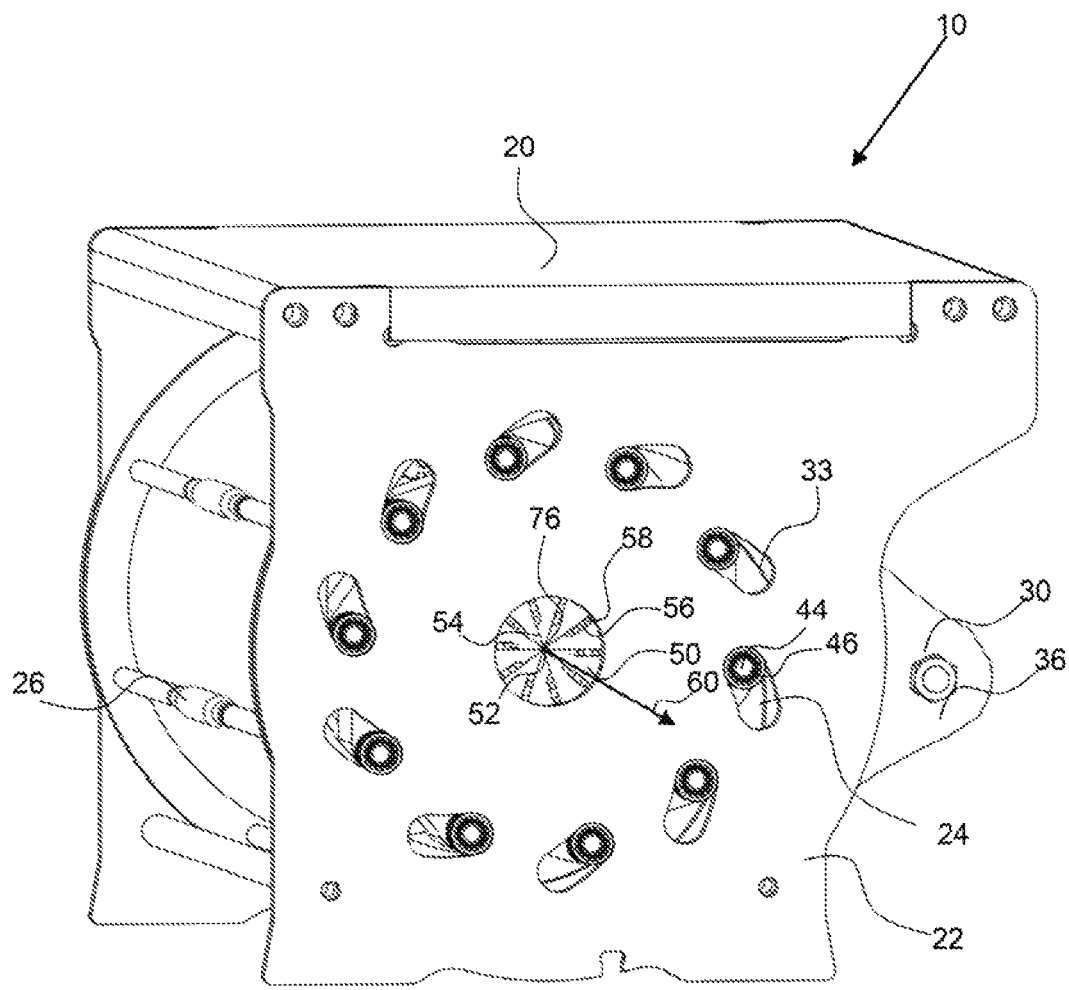
FIG. 2 shows a perspective receiving-side view of an exemplary radial compression mechanism in a closed orientation.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components.

Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Definitions

Referring to FIGS. 1 to 5, an exemplary radial compression mechanism 10 comprises ten compression dies 50 arranged in a circular array forming a cylindrically cavity 70. The compression dies are coupled to a housing 20 having a stationary portion or stationary plate 22 that has guide slots 24, a type of cam guide 33, for directing the motion of the compression dies. A receiving aperture 28 in the stationary plate allows articles to be inserted into the central cylindrical cavity 70 for compression. An exemplary radial compression mechanism may have two housing plates, 22, 22' connected by a plurality of connectors 26.

Figure 5:
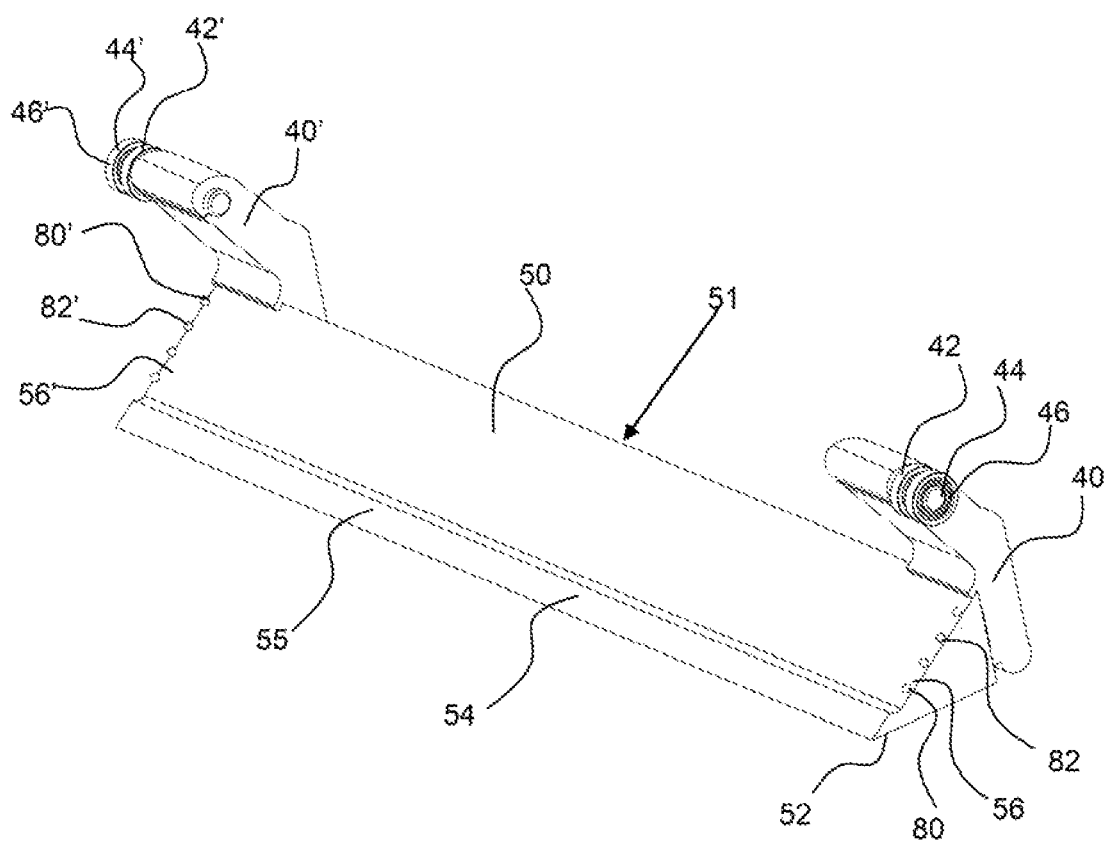
FIG. 5 shows a perspective view of an exemplary complete compression die assembly.

Each compression die 50 has an inward-facing working surface 52 that cooperates with the other dies to form the central cavity, and a back surface 55, as shown in FIG. 5, that interfaces with the working surface of an adjacent compression die. The back surface and working surfaces form interface surfaces between adjacent compression dies and these interface surfaces constrain the dies to have linear motion relative to adjacent dies. The compression dies are constrained in two ways. First, the interface surfaces between adjacent compression dies comprise rolling elements 80, such as die bearing balls 82, that move within a bearing race 56 that extends along the back surface 55 of one of the adjacent compression dies. Second, exemplary compression dies are engaged with a pair of stationary plates on either end, or on opposing sides of the housing 22, 22' as shown in FIG. 1.

The stationary plate or plates comprise cam guides, such as stationary guide slots 24, to guide the motion of cam interfaces 46, such as housing bearings 44 that are retained in the cam guide slots 34. The housing bearings 44 are coupled to the compression dies by a die bearing arm 40 that extends from the compression die and into the guide slots.

The stationary guide slots constrain the compression dies to move approximately radially inward as they are forced to move along the cam guides. A cam portion 30, such as a cam plate, may be coupled to one or more of the cam interfaces and may rotate about the central axis 60 to force the compression dies to move along the cam guides to change the diameter of the central cavity. Note that the plurality of compression dies may be moved along the cam guide by other means, such as a motor coupled with a hub that moves the dies, an actuator and the like. Since the compression dies are constrained to move along the cam guides, any force or movement of one compression die will move the entire mechanism. The exemplary rotating cam plate is engaged with the compression dies by the cam guide slots, which acts as a cam, and is used to drive the dies in unison, whereby the compression dies are driven in unison and the diameter of the central cavity is reduced to close the die. The cam plate rotates about the central cavity and also has cam guide slots for retaining a cam bearing 42 coupled to the compression die. As the center cavity is opened or closed, the motion of each compression die as seen from an adjacent die's reference frame is linear. As each die moves linearly relative to its neighbors as forced by the die-to-die linear bearings. The whole set of dies either rotates relative to the stationary frame about an axis through the center of the central cavity, clockwise or anticlockwise or does not rotate relative to the stationary frame, as determined by the shape of the slot in the stationary plate.

As shown in FIG. 5, an exemplary compression die assembly 51 comprises a wedged shape compression die 50 having a working surface 52 and a back surface 55. A bearing race 56 extends along a portion of the back surface and die bearings 56 are retained between adjacent compression dies, between the race and the working surface of an adjacent compression die. The interface surface 54 extends along the extended end of the compression die and faces the working surface of an adjacent compression die in a die assembly. Die bearing arms 40, 40' extend from the compression die 50 and have a cam bearings 42, 42' and housing bearing 44, 44', respectively, coupled thereto.

Figure 3:
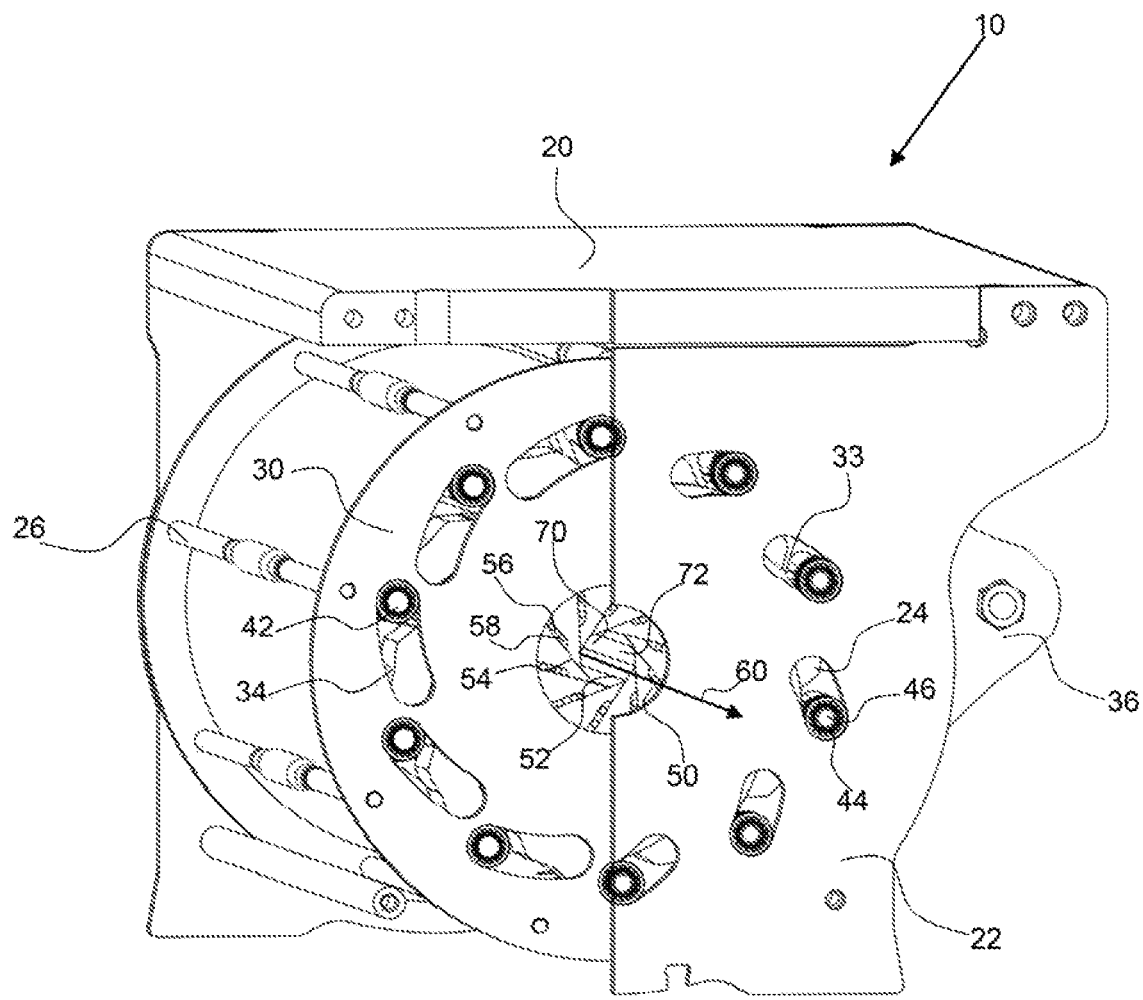
FIG. 3 shows a perspective receiving-side view of an exemplary radial compression mechanism with a portion of the stationary housing plate removed to more clearly show the compression dies, the rotating cam plate and cam bearing as well as the die bearings, bearing balls, between the compression dies.

FIG. 3 shows the stationary plate of the mechanism cut-away to show the rotating cam plate. The shape of the slots in the rotating cam plate determine the relationship between the diameter of the center cavity and the position of the rotating cam plate. In the preferred embodiment, the rotating cam plate is actuated through an actuator arm 36 to which a force is applied by, for example, an air cylinder, a human hand, or an electric motor through a lead screw. A "mechanical advantage" may be produced by the extension of the actuator arm from the central cavity and is the ratio of the radial force applied to the article in the central cavity per amount of actuator force. Longer slots in the rotating cam, or a longer actuator arm attached to the rotating cam, both correspond to a higher mechanical advantage as the mechanism moves from a larger diameter to a smaller diameter central cavity.

Figure 4:
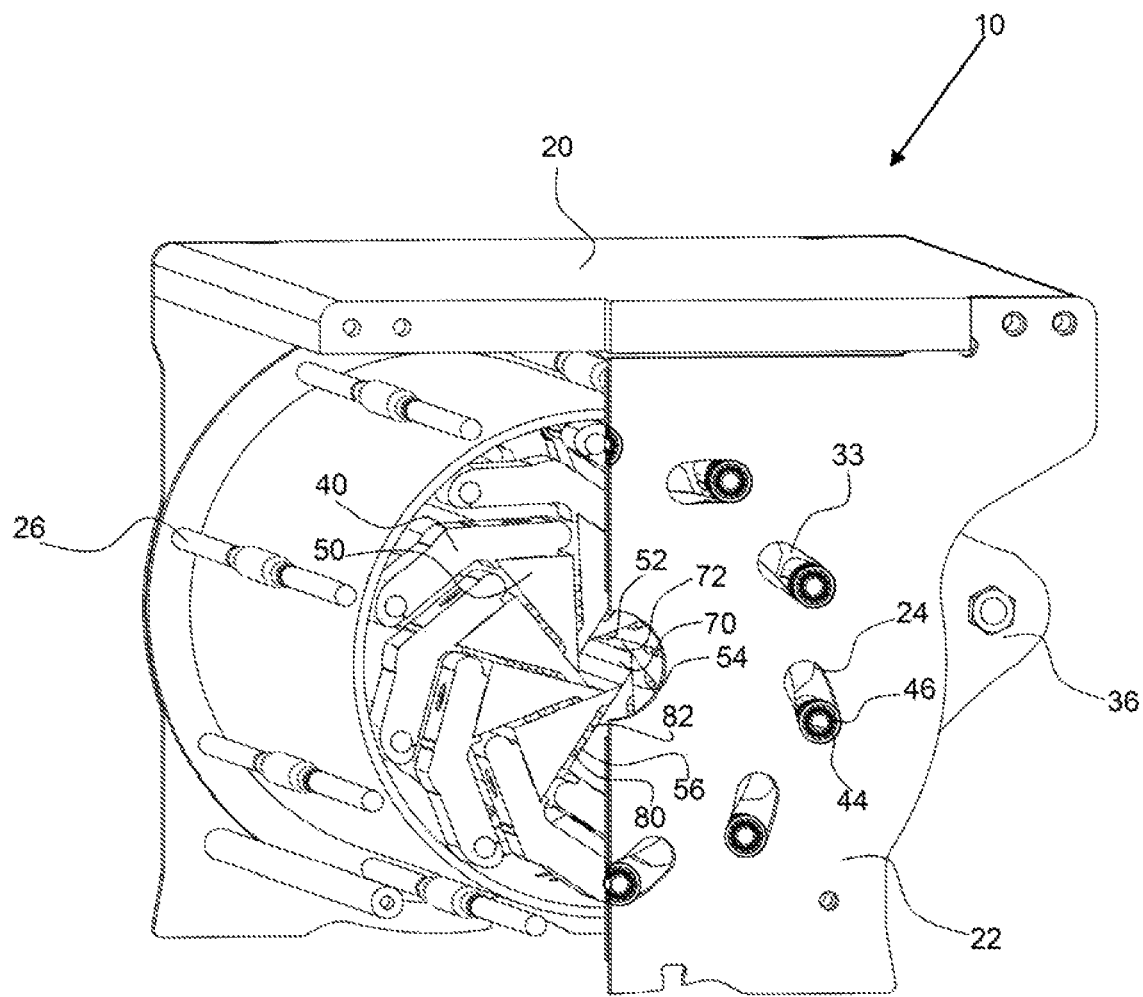
FIG. 4 shows a perspective receiving-side view of an exemplary radial compression mechanism with a portion of the stationary housing plate and cam plate removed to more clearly show the compression die assembly and die bearing arms extending from the wedge shaped compression dies.

As shown in FIG. 4, a portion of the stationary plate and the cam plate are shown in cut-away to provide ease of illustration of the compression die assemblies and the arrangement with respect to these plates. As shown in FIG. 4, a bearing race 56 is configured on the back surface of the compression dies 50 to retain die rolling elements 80, such as die bearings balls 82, therein. The working surface of the adjacent compression die slides along the bearings in the race to provide smooth motion with little friction between the compression dies. The die bearings are used for a die-die interface and guidance. It should be noted that a wide variety of rolling elements may be used including, rolling cylinders, commonly known as needle rollers, die bearing or a combination of these elements. In an exemplary embodiment at least two rolling elements are configured within each bearing race 56 to provide stability of the interface, less wear on the rolling element and bearing race and to distribute the load. The die gaps are influenced only by the size of the race offset in the die and the diameter of the bearing. In an exemplary embodiment a low friction material may be configured between the interface surfaces to allow movement a sliding of the adjacent compression dies along the interface surfaces.

Figure 6:
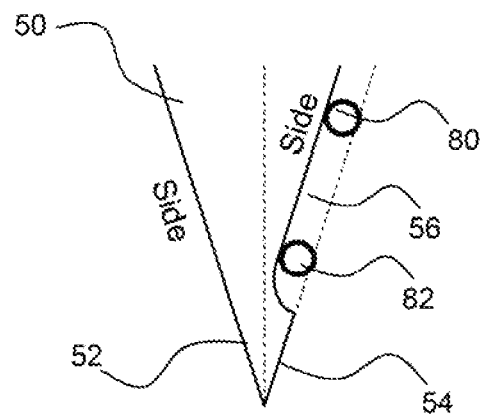
FIG. 6 shows a wedge-shaped die, with and without a bearing race to accommodate die bearing for guidance.
Figure 7:
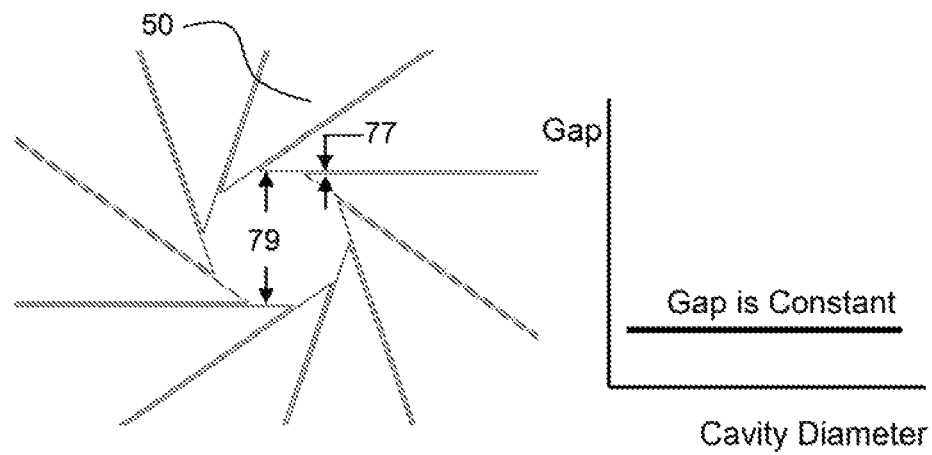
FIG. 7 shows the central cavity portion of an exemplary radial compression mechanism and the relationship between die-to-die gap and cavity diameter.
Figure 8:
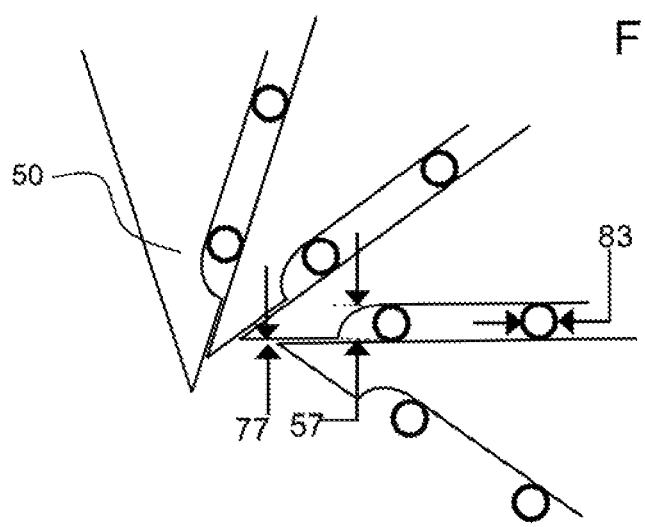
FIG. 8 shows a portion of the central cavity portion of an exemplary radial compression mechanism comprising compression dies having die bearing races for the die bearing to move between the adjacent dies.

Referring now to FIGS. 6 to 8, the linear die to die motion provides a constant die gap throughout the diameter range of the central cavity. The die gap 77 between adjacent dies is determined by the difference between the rolling element diameter, such as the die bearing ball diameter 83 and the race offset 57 dimension. This gap remains constant as the dies move linearly with respect to each other as the diameter of the cylindrical cavity 79 is opened and closed. Again, all of the compression dies may move circumferentially about the central axis as the cylindrical cavity is opened and closed. Each die moves linearly relative to the immediately adjacent dies while, in addition, the whole set of dies either rotates relative to the stationary frame about an axis through the center of the central cavity, either clockwise or anticlockwise or does not rotate relative to the stationary frame, as determined by the shape of the slot in the stationary plate. The rotation may be proportional to the diameter of the center cavity or it may be an arbitrary function of diameter. In the configuration shown in FIGS. 1 through 4, the whole set of dies moves anticlockwise as the central cavity decreases diameter.

Figure 9:
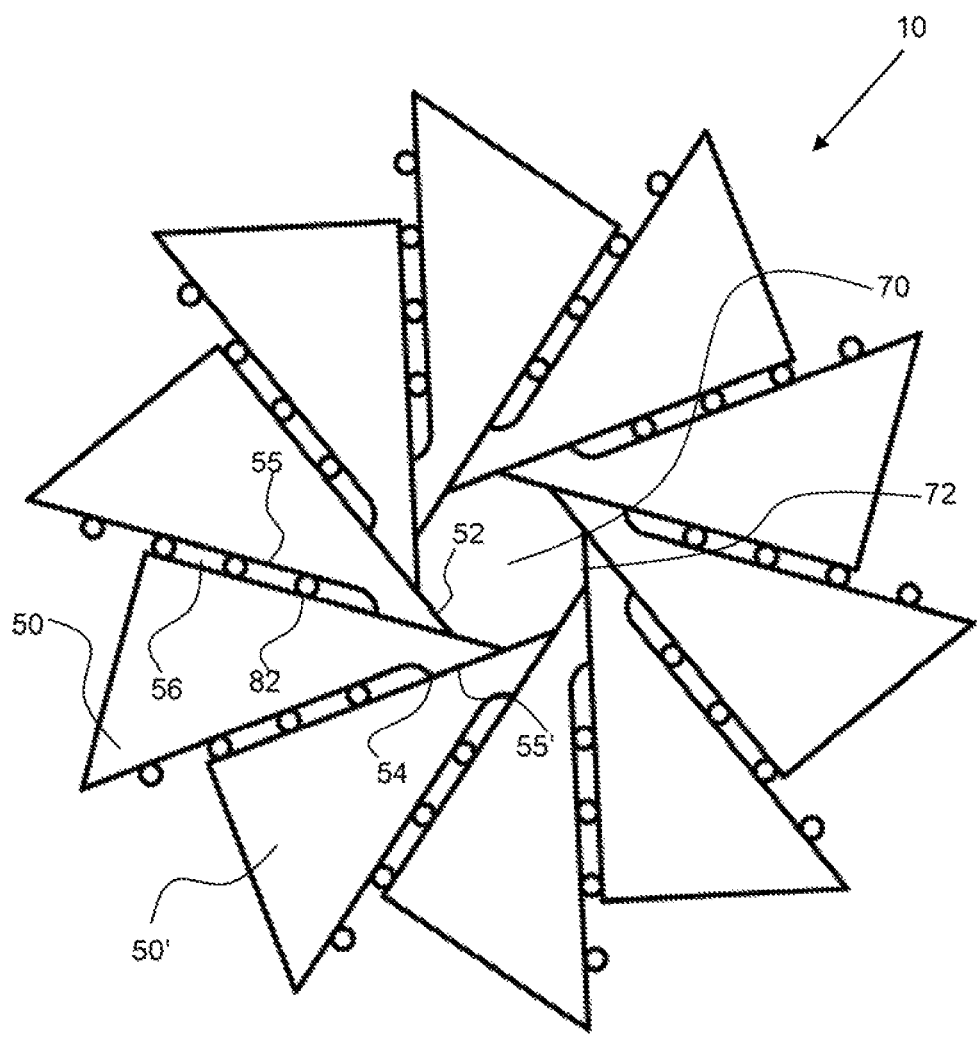
FIG. 9 shows an arrangement of exemplary compression dies configured about a central cavity in an open position.
Figure 10:
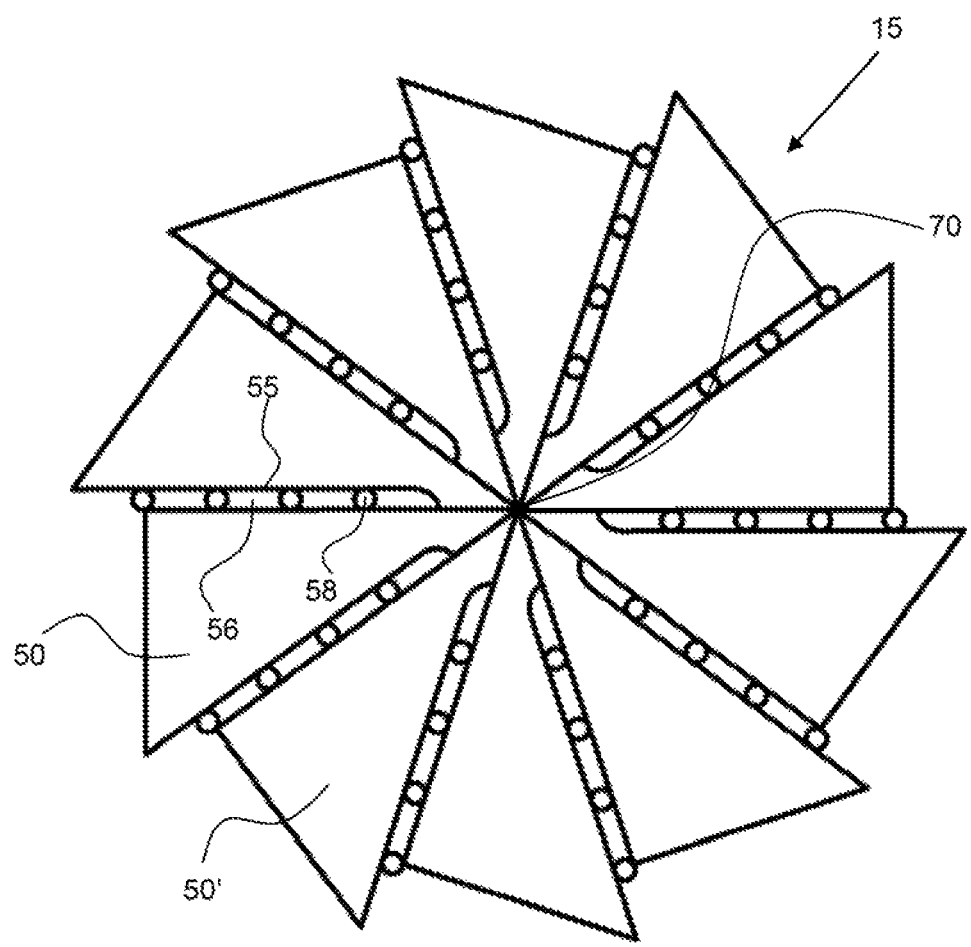
FIG. 10 shows an arrangement of exemplary compression dies configured about a central cavity in a closed position.

Referring to FIGS. 9 and 10, an arrangement of exemplary dies are configured in an open position in FIG. 9 and a closed position in FIG. 10. As shown in FIG. 9, the die bearing races 56 are configured on the back surface 55 of the compression die and the opposing surface is the working surface 52. An interface surface 54 is configured between the back surface and working surface of adjacent compression dies. The working surfaces form the central cylindrical cavity 70 having a cavity surface 72.

Figure 11:
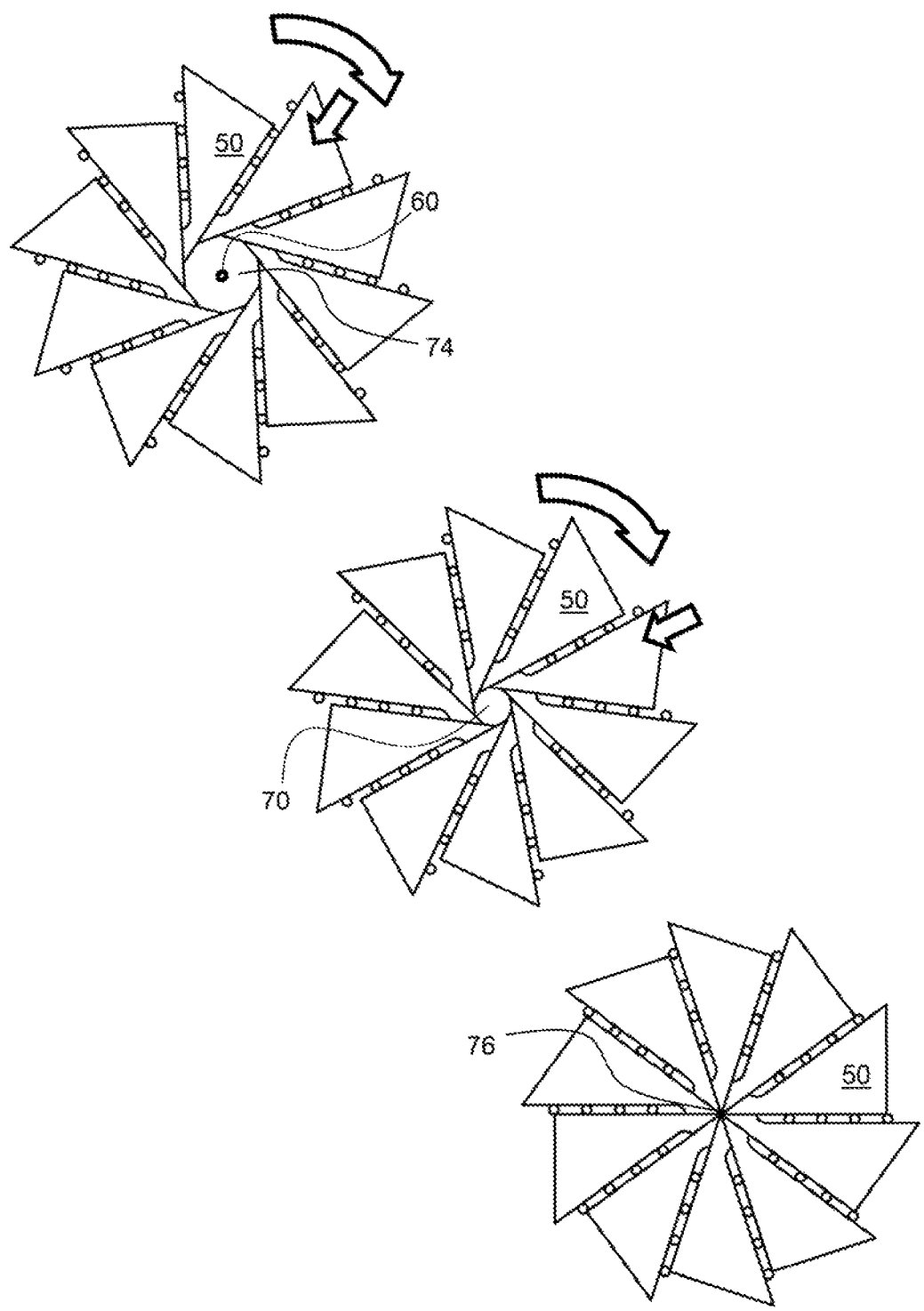
FIG. 11 shows the movement of the compression dies from an open position to a closed position.

As shown in FIG. 11, the plurality of compression dies for a cylindrical cavity 70 that opens and closes as the dies move in a linear motion with respect to each other. As shown, compression die 50 rotates clockwise about the central cavity axis 60 as it moves inward linearly with respect to the adjacent compression dies. The central cavity closes from an open central cavity diameter 74 to a closed central cavity diameter 76.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents

What is claimed is:

1. A radial compression mechanism comprising:
   a) a plurality of dies configured in a circular array, each having a working surface that cooperates with the other dies to form a central cavity having a central axis that is configured to open and close;
   b) an interface surfaces between adjacent dies that constrain the dies to have linear motion relative to adjacent dies; wherein each die has an interface surface that interfaces with an interface surface of an adjacent die,
c) a stationary housing;
d) a cam guide for each of the plurality of dies configured on said stationary housing that constrain the plurality of dies to move from an open position to a closed position;
wherein the cam guide guides the plurality of dies to move as a group in a rotational motion about said central axis while also guiding the plurality of dies to move radially with respect to the central axis;
wherein each of the plurality of dies has a cam interface that restrains the movement of each die as the cam interface moves along the cam guide;
wherein the circular array of the plurality of dies rotates about the central cavity while each of the plurality of dies move in unison radially inward to close the central cavity;
wherein the plurality of dies are constrained in motion from an open position to a closed position by the interface surface between adjacent dies and the cam guide; and
wherein the plurality of dies are coupled to said housing and configured to move in unison from an open position, wherein the central cavity is in an open position having an open cavity diameter, to a closed position, wherein the cylindrical cavity is in a closed position having a closed cavity diameter;
wherein said open cavity diameter is larger than said closed cavity diameter.

2. The radial compression mechanism of claim 1, wherein the cam guide guides have a curved shape.

3. The radial compression mechanism of claim 2, wherein the plurality of cam guides are cam guide slots.

4. The radial compression mechanism of claim 3, wherein each of the plurality of dies comprises a bearing arm that extends into a respective cam slot to guide the plurality of dies to move in a rotational motion about said central axis.

5. The radial compression mechanism of claim 3, wherein each of the bearing arms comprises a housing bearing that moves within the cam guide slots.

6. The radial compression mechanism of claim 1, wherein each of the plurality of dies have a bearing race having a race offset distance that extends along at least a portion of the interface surface between adjacent dies; and wherein the radial compression mechanism comprises at least two rolling elements that are configured in said bearing race.

7. The radial compression mechanism of claim 6, wherein the at least two rolling elements are balls.

8. The radial compression mechanism of claim 6, wherein the at least two rolling elements are needle rollers.

9. The radial compression mechanism of claim 6, wherein a die gap is configured between adjacent dies having a die gap dimension that is the difference between the race offset and a diameter of the rolling element.

10. The radial compression mechanism of claim 9, wherein the die gap dimension is no more than about 0.2 mm.

11. The radial compression mechanism of claim 1, comprising three or more dies.

12. The radial compression mechanism of claim 1, comprising between three and fifteen dies.

13. The radial compression mechanism of claim 1, further comprising a cam actuator that moves the plurality of dies to move along the cam guides.

14. The radial compression mechanism of claim 13, wherein the cam actuator comprises a cam plate that rotates about the central cavity to drive plurality of dies to move along the cam guides.

* * * * *